United States Patent [19]
Cervantes et al.

[11] Patent Number: 5,925,341
[45] Date of Patent: Jul. 20, 1999

[54] NANOEMULSION BASED ON NONIONIC AMPHIPHILIC LIPIDS AND AMINATED SILICONES AND USES

[75] Inventors: Frédéric Cervantes, Paris; Bénédicte Cazin, Clichy; Jean-Thierry Simonnet, Paris, all of France

[73] Assignee: L'Oreal, Paris, France

[21] Appl. No.: 09/042,557

[22] Filed: Mar. 17, 1998

[30]    Foreign Application Priority Data

Mar. 18, 1997 [FR] France ..................... 97 03283

[51] Int. Cl.⁶ ................. A61K 7/00; A61K 7/48
[52] U.S. Cl. ................. 424/78.03; 424/70.12; 424/70.122; 514/937; 514/938
[58] Field of Search ............. 424/78.03, 70.12, 424/70.122; 514/937, 938

[56] References Cited

U.S. PATENT DOCUMENTS

| | | | |
|---|---|---|---|
| 4,529,586 | 7/1985 | De Marco et al. ............ | 424/70 |
| 5,098,745 | 3/1992 | Gordon ................... | 427/355 |
| 5,244,598 | 9/1993 | Merrifield et al. | |
| 5,518,716 | 5/1996 | Merrifield et al. | |

FOREIGN PATENT DOCUMENTS

| | | |
|---|---|---|
| 0 514 934 | 11/1992 | European Pat. Off. . |
| 0 529 883 | 3/1993 | European Pat. Off. . |
| 0 674 898 | 10/1995 | European Pat. Off. . |
| 5-151120 | 6/1993 | Japan . |
| WO 94/22420 | 10/1994 | WIPO . |
| WO 95/15742 | 6/1995 | WIPO . |

*Primary Examiner*—Sally Gardner-Lane
*Attorney, Agent, or Firm*—Finnegan, Henderson, Farabow, Garrett & Dunner, L.L.P.

[57] ABSTRACT

An oil-in-water emulsion with oil globules with a mean size of no greater than 150 nm, comprising an amphiphilic lipid phase comprising at least one nonionic amphiphilic lipid which is liquid at an ambient temperature of less than 45° C., at least one oil and at least one aminated silicone, as well as to its uses in the cosmetic or dermopharmaceutical field.

39 Claims, No Drawings

NANOEMULSION BASED ON NONIONIC AMPHIPHILIC LIPIDS AND AMINATED SILICONES AND USES

The present invention relates to an oil-in-water emulsion whose oil globules have a mean size of no greater than 150 nm and which comprises at least one oil, at least one aminated silicone and an amphiphilic lipid phase based on nonionic amphiphilic lipids which are liquid at an ambient temperature of less than 45° C., as well as to their use, as a topical application, particularly in the cosmetic and dermopharmaceutical fields.

According to the invention, nanoemulsions refer to emulsions whose oil globules have a mean size of no greater than 150 nm (nanometers).

Oil-in-water emulsions are well known in the cosmetic and dermopharmaceutical field particularly for the preparation of cosmetic products such as lotions, tonics, serums, and toilet water.

However, the presence of high concentrations of vegetable, animal or mineral oils in some compositions makes their formulation difficult. Indeed, the compositions are generally unstable during storage and the cosmetic properties are inadequate. In particular, the application of such compositions to the hair leads to a greasy feel and difficulty in rinsing. Furthermore, the dried hair lacks volume and has a charged feel.

Nanoemulsions comprising an amphiphilic lipid phase comprising phospholipids, a cationic lipid, water and a hydrophobic sunscreen are known in the state of the art. They are obtained by a high-pressure homogenization process. These emulsions have the disadvantage of being unstable during storage at the traditional storage temperatures, namely from 0 to 45° C. They lead to yellow compositions and produce rancid odors which develop after a few days of storage. Furthermore, these emulsions do not provide good cosmetic properties. They are described in the "DCI" review of April 1996, pages 46–48.

The inventors have discovered, unexpectedly, new emulsions whose oil globules have a mean size of no greater than 150 nm and which are stable during storage from 0 to 45° C. after at least one month. The emulsions in accordance with the invention can be prepared at temperatures ranging from 20 to 45° C. and are compatible with heat-sensitive active agents. They may contain large quantities of oil. They may in particular contain large quantities of perfume and may enhance their persistence. They also promote the penetration of active agents into the top layers of the skin and the deposition of active agent on keratinous fibers such as hair. Hair treated with these emulsions is sleek and glossy without having a greasy feel or appearance, it disentangles easily and is soft and light.

A subject of the present invention is oil-in-water emulsions comprising an oily phase dispersed in an aqueous phase, having oil globules whose mean size is no greater than 150 nm, characterized in that they comprise at least one oil, at least one aminated silicone and an amphiphilic lipid phase which comprises at least one nonionic amphiphilic lipid which is liquid at an ambient temperature of less than 45° C., and in that the weight ratio of the quantity of oily phase to the quantity of amphiphilic lipid phase preferably ranges from 2:1 to 10:1, more preferably from 2:1 to 8:1, and even more preferably from 2:1 to 6:1.

Advantageously, the ratio by weight of the quantity of oily phase in these emulsions to the amphiphilic lipid phase varies from 1:1 to 10:1, and more preferably from 2:1 to 8:1.

Advantageously, the aminated silicone is present in an amount preferably ranging from 0.05 to 10% by weight relative to the total weight of the emulsion, more preferably from 0.1 to 5% by weight.

The nonionic amphiphilic lipids of the invention are preferably selected from silicone surfactants and esters of at least one polyol selected from: polyethylene glycol containing from 1 to 60 ethylene oxide units; sorbitan; glycerol containing from 2 to 30 ethylene oxide units; and polyglycerols containing from 2 to 15 glycerol units, and of at least one fatty acid containing at least one saturated or unsaturated, linear or branched $C_8$–$C_{22}$ alkyl chain. It is also possible to use mixtures of the above compounds.

The silicone surfactants which can be used according to the invention are silicone compounds containing at least one oxyethylenated chain —$OCH_2CH_2$— and/or oxypropylenated chain —$OCH_2CH_2CH_2$—. As silicone surfactants which can be used according to the invention, there may be mentioned those described in U.S. Pat. Nos. 5,364,633 and 5,411,744, the disclosures of which are specifically incorporated by reference herein.

Preferably, the silicone surfactant used according to the present invention is a compound of formula (I):

$$R_1-\underset{\underset{CH_3}{|}}{\overset{\overset{CH_3}{|}}{Si}}O-\left[\underset{\underset{CH_3}{|}}{\overset{\overset{CH_3}{|}}{Si}}O\right]_A-\left[\underset{\underset{R_2}{|}}{\overset{\overset{CH_3}{|}}{Si}}O\right]_B-\underset{\underset{CH_3}{|}}{\overset{\overset{CH_3}{|}}{Si}}-R_3$$

in which:

$R_1$, $R_2$, and $R_3$ independently represent a $C_1$–$C_6$ alkyl radical or a radical —$(CH_2)_x$—$(OCH_2CH_2)_y$—$(OCH_2CH_2CH_2)_z$—$OR_4$, wherein at least one $R_1$, $R_2$, or $R_3$ radical is not an alkyl radical; wherein $R_4$ is selected from hydrogen, an alkyl radical and an acyl radical;

A is an integer ranging from 0 to 200;

B is an integer ranging from 0 to 50;

with the proviso that A and B are not simultaneously equal to 0;

X is an integer independently ranging from 1 to 6;

Y is an integer independently ranging from 1 to 30; and

Z is an integer independently ranging from 0 to 5.

According to a preferred embodiment of the invention, in the compound of formula (I), the alkyl radical is a methyl radical, X is an integer independently ranging from 2 to 6 and Y is an integer independently ranging from 4 to 30.

There may be mentioned, by way of example of silicone surfactants of formula (I), the compounds of formula (II):

$$(CH_3)_3SiO-[(CH_3)_2SiO]_A-(CH_3SiO)_B-Si(CH_3)_3$$
$$|$$
$$(CH_2)_2-(OCH_2CH_2)_y-OH$$

(II)

in which:

A is an integer ranging from 20 to 105;

B is an integer ranging from 2 to 10; and

Y is an integer ranging from 10 to 20.

It is also possible to mention, by way of example of silicone surfactants of formula (I), the compounds of formula (III):

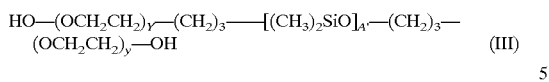

(III)

in which:

A' and Y each independently represent an integer ranging from 10 to 20.

It is also possible to use as compounds of the invention those marketed by the company Dow Corning under the names DC 5329, DC 7439-146, DC 2-5695, and Q4-3667. The compounds DC 5329, DC 7439-146, and DC 2-5695 are compounds of formula (II) where, respectively, A is about 22, B is about 2 and Y is about 12; A is about 103, B is about 10, and Y is about 12; A is about 27, B is about 3 and Y is about 12.

The compound Q4-3667 is a compound of formula (III) where A is about 15 and Y is about 13.

Among the nonionic amphiphilic lipids, there may be mentioned more particularly, by way of example:

polyethylene glycol isostearate (having about 8 ethylene glycol units) of number average molecular weight about 400, diglyceryl isostearate, polyglycerol laurate containing about 10 glycerol units, sorbitan oleate, sorbitan isostearate, and α-butylglucoside cocoate or α-butylglocoside caprate.

According to an essential characteristic of the compositions in accordance with the invention, the emulsions contain at least one aminated silicone.

Throughout the following and preceding text, silicone or polysiloxane are intended to designate, in accordance with what is generally accepted, any organosilicon-containing polymer or oligomer with a branched or cross-linked, linear or cyclic structure, of variable molecular weight, which are obtained by polymerization and/or polycondensation of suitably functionalized silanes, and which comprise a repetition of principal units in which the silicon atoms are linked to each other by oxygen atoms (siloxane bond ≡Si—O—Si≡), optionally substituted hydrocarbon radicals being directly linked via a carbon atom on the silicon atoms. The most common hydrocarbon radicals are alkyl radicals, particularly $C_1$–$C_{10}$ and in particular methyl, fluoroalkyl radicals, aryl radicals and in particular phenyl, and alkenyl radicals and in particular vinyl; other types of radicals capable of being linked, either directly or via a hydrocarbon radical, to the siloxane chain are particularly hydrogen, halogens and in particular chlorine, bromine or fluorine, thiols, alkoxy radicals, polyoxyalkylene (or polyether) radicals and in particular polyoxyethylene and/or polyoxypropylene, hydroxyl or hydroxyalkyl radicals, amide groups, acyloxy or acyloxyalkyl radicals, amphoteric or betaine groups, anionic groups such as carboxylates, thioglycolates, sulphosuccinates, thiosulphates, phosphates and sulphates, this list of course not being at all limiting (so-called "organomodified" silicones).

According to the invention, aminated silicone designates any silicone comprising at least one primary, secondary, or tertiary amine or quaternary ammonium group. There may thus be mentioned:

(a) the polysiloxanes called in the CTFA dictionary "amodimethicone" and corresponding to the formula (IV):

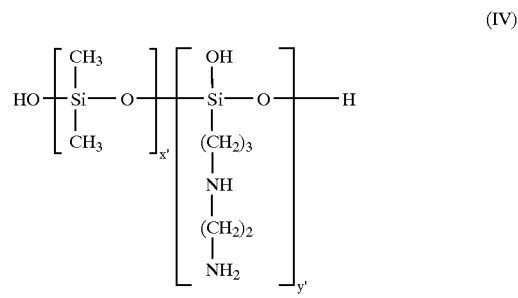

in which:

x' and y' independently are integers depending on the molecular weight, generally such that the weight-average molecular weight ranges from 5000 to 500,000;

(b) the aminated silicones corresponding to the formula (V):

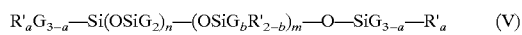

in which:

G independently denotes a hydrogen atom or a phenyl, OH, or $C_1$–$C_8$ alkyl, for example methyl;

a denotes the number 0 or an integer ranging from 1 to 3, in particular 0;

b denotes 0 or 1, and in particular, 1;

m and n are numbers such that the sum (m+n) may vary preferably from 1 to 2000 and more preferably from 50 to 150, it being possible for n to denote a number from 0 to 1999 and in particular from 49 to 149 and it being possible for m to denote a number from 1 to 2000 and in particular 1 to 10;

R' is a monovalent radical of formula —$C_qH_{2q}$L in which q independently denotes a number from 2 to 8 and L is an optionally quaternized amine group selected from:

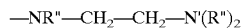

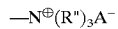

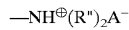

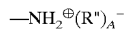

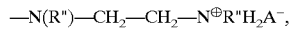

in which R" designates hydrogen, phenyl, benzyl or a monovalent saturated hydrocarbon radical, for example an alkyl radical having from 1 to 20 carbon atoms, and A⁻ represents a halide ion such as, for example, fluoride, chloride, bromide-, or iodide.

A product corresponding to this definition is the silicone called "trimethylsilylamodimethicone", "corresponding to the formula (VI):

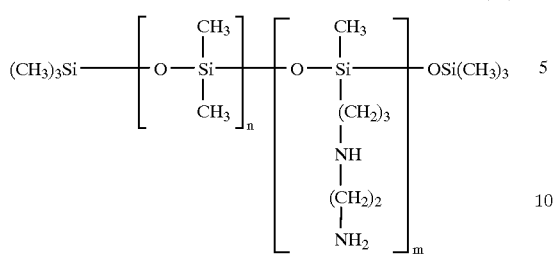

in which:

n and m have the meanings given above in formula (V).

Such polymers are described for example in Patent Application EP-A-95238, the disclosure of which is specifically incorporated by reference herein.

(c) the aminated silicones corresponding to the formula (VII):

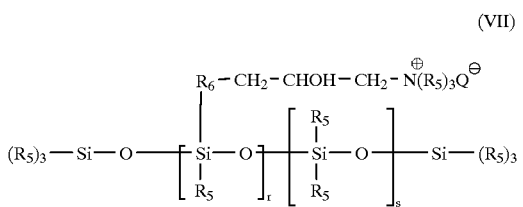

in which:

$R_5$ independently represents a monovalent hydrocarbon radical having from 1 to 18 carbon atoms, and in particular a $C_1$–$C_{18}$ alkyl radical, or a $C_2$–$C_{18}$ alkenyl radical, for example, methyl;

$R_6$ independently represents a divalent hydrocarbon radical, in particular a $C_1$–$C_{18}$ alkylene radical or a divalent $C_1$–$C_{18}$ alkyleneoxy radical, for example $C_1$–$C_8$ linked to Si by an SiC bond;

$Q^-$ is an anion such as a halide ion, in particular chloride or an organic acid salt (acetate and the like);

r represents a mean statistical value from 2 to 20, and in particular from 2 to 8; and s represents a mean statistical value from 20 to 200, and in particular from 20 to 50.

Such aminated silicones are described more particularly in U.S. Pat. No. 4,185,087, the disclosure of which is specifically incorporated by reference herein.

A silicone entering into this class is the silicone marketed by the company Union Carbide under the name "UCAR SILICONE ALE 56".

d) the quaternary ammonium silicones of formula (VIIb):

in which $R_7$ independently represent a monovalent hydrocarbon radical having from 1 to 18 carbon atoms, and in particular a $C_1$–$C_{18}$ alkyl radical, a $C_2$–$C_{18}$ alkenyl radical or a ring comprising 5 or 6 carbon atoms, for example methyl;

$R_6$ independently represents a divalent hydrocarbon radical, in particular a $C_1$–$C_{18}$ alkylene radical or a divalent $C_1$–$C_{18}$ alkyleneoxy radical, for example $C_1$–$C_8$ linked to Si by an SiC bond;

$R_8$ independently represent a hydrogen atom, a monovalent hydrocarbon radical having 1 to 18 carbon atoms, and in particular a $C_1$–$C_{18}$ alkyl radical, a $C_2$–$C_{18}$ alkenyl radical, a radical —$R_6$—NHCOR$_7$;

$X^-$ is an anion such as a halide ion, in particular chloride, or an organic acid salt (acetate and the like);

r represents a mean statistical value from 2 to 200, and in particular from 5 to 100.

These silicones are, for example, described in EP-A-0 530,974, the disclosure of which is specifically incorporated by reference herein.

Silicones entering into this class are the silicones marketed by the company GOLDSCHMIDT under the names ABIL QUAT 3270, ABIL QUAT 3272, and ABIL QUAT 3474.

According to the invention, the aminated silicones may be provided in the form of an oil or of aqueous, alcoholic or aqueous-alcoholic solutions, or in the form of a dispersion or emulsion.

A particularly advantageous embodiment is their use in the form of emulsions, in particular in the form of microemulsions or nanoemulsions.

It is known to use, for example, the product marketed under the name "EMULSION CATIONIQUE DC 929" by the company Dow Corning which comprises, in addition to the amodimethicone, a cationic surface-active agent derived from tallow fatty acids called Tallowtrimonium (CTFA), in combination with a nonionic surface-active agent known under the name "Nonoxynol 10".

It is also possible to use, for example, the product marketed under the name "EMULSION CATIONIQUE DC 939" by the company Dow Corning comprising, in addition to the amodimethicone, a cationic surface-active agent trimethylcetylammonium chloride in combination with a nonionic surface-active agent tridecth-12.

Another commercial product which can be used according to the invention is the product marketed under the name "DOW CORNING Q2 7224" by the company Dow Corning comprising, in combination, the trimethylsilylamodimethicone of formula (IV), a nonionic surface-active agent of formula: $C_8H_{17}$—$C_6H_4$—(OCH$_2$CH$_2$)$_n$—OH where n=40, also called octoxynol-40, another nonionic surface-active agent of formula: $C_{12}H_{25}$—(OCH$_2$—CH$_2$)$_n$—OH where n=6, also called isolaureth-6, and glycol.

(VIIb)

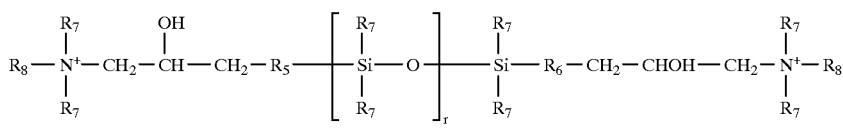

Advantageously, the aminated silicone is present in an amount preferably ranging from 0.05 to 10% by weight, relative to the total weight of the emulsion, more preferably ranging from 0.1 to 5% by weight and even more preferably ranging from 0.3 to 3% by weight.

A specific form of emulsion in accordance with the invention is characterized in that the amphiphilic lipid phase additionally comprises one or more ionic amphiphilic lipids.

The ionic amphiphilic lipids used in the emulsions of the invention are preferably selected from anionic lipids, amphoteric lipids and more preferably cationic lipids.

The anionic amphiphilic lipids are more particularly selected from:

alkali metal salts of dicetyl- and dimyristylphosphate;

alkali metal salts of cholesterol sulphate;

alkali metal salts of cholesterol phosphate;

lipoamino acids such as mono- and disodium acyl glutamates;

sodium salts of phosphatidic acid;

phosopholipids; and alkylsulphonic derivatives such as those of the formula:

$$R-CH(SO_3M)-CO-O-(CH_2-CH_2-CO)--CH_3$$

in which:

R represents $C_1$–$C_{22}$ alkyl radicals, in particular $C_{16}H_{33}$ and $C_{18}H_{37}$ radicals, taken in the form of a mixture or separately, and M is an alkali metal such as sodium.

The cationic amphiphilic lipids used in the emulsions of the invention are preferably selected from quaternary ammonium salts, fatty amines and salts thereof.

The quaternary ammonium salts are, for example:

those which have the following formula (VIII):

$$\left[ \begin{array}{c} R_1 \\ R_2 \end{array} N \begin{array}{c} R_3 \\ R_4 \end{array} \right]^+ X^-  \quad (VIII)$$

in which:

the radicals $R_1$ to $R_4$ independently represent a linear or branched aliphatic radical containing 1 to 30 carbon atoms, or an aromatic radical such as aryl or alkylaryl. The aliphatic radicals may contain heteroatoms such as in particular oxygen, nitrogen, sulphur, or halogens. The aliphatic radicals are selected, for example, from the alkyl, alkoxy, polyoxy($C_2$–$C_6$)-alkylene, alkylamide, ($C_{12}$–$C_{22}$)alkylamido($C_2$–$C_6$)alkyl, ($C_{12}$–$C_{22}$)alkyl acetate or hydroxyalkyl radicals containing from about 1 to 30 carbon atoms;

X is an anion selected from halides, phosphates, acetates, lactates, ($C_2$–$C_6$)alkyl sulphates and alkyl- or alkylarylsulphonates, the quaternary ammonium salts of imidazolinium, such as, for example, those of formula (IX):

$$\left[ \begin{array}{c} R_6 \\ \text{imidazolinium ring with } R_7 \end{array} N-CH_2-CH_2-N(R_8)-CO-R_5 \right]^+ X^- \quad (IX)$$

in which:

$R_5$ represents an alkenyl or alkyl radical containing from 8 to 30 carbon atoms which are for example derived from tallow fatty acids, $R_6$ represents a hydrogen atom, a $C_1$–$C_4$ alkyl radical or an alkenyl or alkyl radical containing from 8 to 30 carbon atoms, $R_7$ represents a $C_1$–$C_4$ alkyl radical, $R_8$ represents a hydrogen atom, a $C_1$–$C_4$ alkyl radical, X is an anion selected from halides, phosphates, acetates, lactates, alkyl sulphates, and alkyl- or alkylarylsulphonates.

Preferably $R_5$ and $R_6$ designate a mixture of alkenyl or alkyl radicals containing from 12 to 21 carbon atoms which are for example derived from tallow fatty acids, $R_7$ designates methyl and $R_8$ designates hydrogen. Such a product is, for example, marketed under the name "REWOQUAT W 75" by the company REWO, the quaternary diammonium salts of formula (X):

$$\left[ R_9 - \underset{R_{11}}{\overset{R_{10}}{N}} - (CH_2)_3 - \underset{R_{13}}{\overset{R_{12}}{N}} - R_{14} \right]^{++} 2X^- \quad (X)$$

in which:

$R_9$ designates an aliphatic radical containing from about 16 to 30 carbon atoms, $R_{10}$, $R_{11}$, $R_{12}$, $R_{13}$, and $R_{14}$ independently are selected from hydrogen and an alkyl radical containing 1 to 4 carbon atoms, and X is an anion selected from halides, acetates, phosphates, nitrate and methyl sulphates. Such quaternary diammonium salts comprise in particular propanetallowdiammonium dichloride, the quaternary ammonium salts containing at least one ester functional group.

The quaternary ammonium salts containing at least one ester functional group which can be used according to the invention are for example those of the following formula (XI):

$$R_{17}-\overset{O}{\underset{}{C}}-(OC_nH_{2n})_y-\underset{R_{15}}{\overset{(C_rH_{2r}O)_z-R_{18}}{N^+}}-(C_pH_{2p}O)_x-R_{16}, \quad X^- \quad (XI)$$

in which:

$R_{15}$ is selected from $C_1$–$C_6$ alkyl radicals and $C_1$–$C_6$ hydroxyalkyl or dihydroxyalkyl radicals;

$R_{16}$ is selected from:
the radical

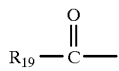

the saturated or unsaturated, linear or branched $C_1$–$C_{22}$ hydrocarbon radicals $R_{20}$,
the hydrogen atom,
$R_{18}$ is selected from:
the radical

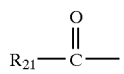

the saturated or unsaturated, linear or branched $C_1$–$C_6$ hydrocarbon radicals $R_{22}$,
the hydrogen atom,
$R_{17}$, $R_{19}$, and $R_{21}$ independently are selected from the saturated or unsaturated, linear or branched $C_7$–$C_{21}$, hydrocarbon radicals;
n, p and r independently denote integers ranging from 2 to 6;
y is an integer ranging from 1 to 10;
x and z independently denote integers ranging from 0 to 10;
X⁻ is an organic or inorganic, simple or complex anion; with the proviso that the sum x+y+z has a value ranging from 1 to 15, that when x has a value of 0, then $R_{16}$ designates $R_{20}$, and that when z has a value of 0, then $R_{18}$ designates $R_{22}$.

The alkyl radicals $R_{15}$ may be linear or branched and more particularly linear.

Preferably, $R_{15}$ denotes a methyl, ethyl, hydroxyethyl or dihydroxypropyl radical and more preferably a methyl or ethyl radical.

Advantageously, the sum x+y+z has a value ranging from 1 to 10.

When $R_{16}$ is a hydrocarbon radical $R_{20}$, it may be long and may have from 12 to 22 carbon atoms, or may be short and may have from 1 to 3 carbon atoms.

When $R_{18}$ is a hydrocarbon radical $R_{22}$, it preferably has from 1 to 3 carbon atoms.

Advantageously, $R_{17}$, $R_{19}$, and $R_{21}$ are independently selected from saturated or unsaturated, linear or branched $C_{11}$–$C_{21}$ hydrocarbon radicals, and more particularly from saturated or unsaturated, linear or branched $C_{11}$–$C_{21}$ alkyl and alkenyl radicals.

Preferably, x and z independently have a value of 0 or 1.
Advantageously, y is equal to 1.
Preferably, n, p, and r independently denote 2 or 3, and still more preferably, are equal to 2.

The anion is preferably a halide (chloride, bromide, or iodide) or an alkyl sulphate, more particularly methyl sulphate. It is however possible to use methanesulphonate, phosphate, nitrate, tosylate, and an organic acid-derived anion such as acetate or lactate or any other anion compatible with ammonium containing an ester functional group.

The anion X⁻ is still more particularly chloride or methyl sulphate.

Use is more particularly made of the ammonium salts of formula (XI) in which:

$R_{15}$ denotes a methyl or ethyl radical,
x and y are independently equal to 1,;
z is equal to 0 or 1;
n, p ,and r are equal to 2;
$R_{16}$ is selected from:
the radical

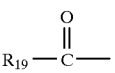

the methyl, ethyl or $C_{14}$–$C_{22}$ hydrocarbon radicals, and the hydrogen atom,
$R_{18}$ is selected from
the radical

and the hydrogen atom,:
$R_{17}$, $R_{19}$, and $R_{21}$ are independently selected from saturated or unsaturated, linear or branched $C_{13}$–$C_{17}$ hydrocarbon radicals and preferably from saturated or unsaturated, linear or branched $C_{13}$–$C_{17}$ alkyl and alkenyl radicals.

Advantageously, the hydrocarbon radicals are linear.

There may be mentioned, for example, the compounds of formula (XI) such as the salts (chloride or methyl sulphate in particular) of diacyloxyethyldimethylammonium, of diacyloxyethylhydroxyethylmethylammonium, of monoacyloxyethyldihydroxyethylmethylammonium, of triacyloxyethylmethylammoni m, of monoacyloxyethylhydroxyethyldimethylammonium and mixtures thereof. The acyl radicals preferably have from 14 to 18 carbon atoms and are more particularly obtained from a vegetable oil such as palm oil or sunflower oil. When the compound contains several acyl radicals, the latter may be identical or different.

These products are obtained for example by direct esterification of triethanolamine, of triisopropanolamine, of alkyldiethanolamine or of alkyldiisopropanolamine which are optionally oxyalkylenated and of fatty acids or of mixtures of fatty acids of plant or animal origin or by transesterification of methyl esters thereof. This esterification is followed by quaternization with the aid of an alkylating agent such as an alkyl (preferably methyl or ethyl) halide, a dialkyl (preferably methyl or ethyl) sulphate, methyl methanesulphonate, methyl para-toluenesulphonate, or glycol or glycerol chlorohydrin.

Such compounds are for example marketed under the names DEHYQUART by the company HENKEL, STEPANQUAT by the company STEPAN, NOXAMIUM by the company CECA, REWOQUAT WE 18 by the company REWO-WITCO.

The composition according to the invention preferably contains a mixture of quaternary ammonium mono-, di- and triester salts, with a majority by weight of diester salts.

As a mixture of ammonium salts, there may be used for example the mixture containing from 15 to 30% by weight of acyloxyethyldihydroxyethylmethylammonium methyl sulphate, from 45 to 60% of diacyloxyethylhydroxyethylmethylammonium methyl sulphate, and from 15 to 30% of triacyloxyethylmethylammonium methyl sulphate, acyl radicals having from 14 to 18 carbon atoms and obtained from optionally partially hydrogenated palm oil.

It is also possible to use the ammonium salts containing at least one ester functional group which are described in U.S. Pat. Nos. 4,874,554 and 4,137,180, the disclosures of which are specifically incorporated by reference herein.

Among the quaternary ammonium salts of formula (VIII), there are preferred, on the one hand, the tetraalkylammonium chlorides such as for example the dialkyldimethylammonium or alkyltrimethylammonium chlorides, in which the alkyl radical contains from about 12 to 22 carbon atoms, in particular, the behenyltrimethylammonium, distearyldimethylammonium, cetyltrimethylammonium and benzyldimethylstearylammonium chlorides or alternatively, on the other hand, the stearamidopropyldimethyl(myristyl acetate) ammonium chloride marketed under the name "CERAPHYL 70" by the company VAN DYK.

According to the invention, the behenyltrimethylammonium chloride is the quaternary ammonium salt most particularly preferred.

The amphiphilic ionic lipids are present in the emulsions of the invention preferably in an amount ranging from 0 to 60% by weight and more preferably from 10 to 50% by weight, relative to the total weight of the amphiphilic lipid phase.

Advantageously, the amphiphilic ionic lipids are present in the emulsions of the invention in an amount ranging from 0 to 10% by weight, more preferably from 0.05 to 5% by weight, and even more preferably from 0.5 to 3% by weight relative to the total weight of the emulsion.

The emulsions in accordance with the invention contain a quantity of oil preferably ranging from 5 to 40% by weight relative to the total weight of the emulsion and more preferably from 8 to 30% by weight.

The oils which can be used in the emulsions of the invention are preferably selected from:

- the animal or vegetable oils formed by esters of fatty acids and of polyols, in particular liquid triglycerides, for example sunflower, maize, soybean, avocado, jojoba, gourd, grapeseed, sesame and hazelnut oils, fish oils, glycerol tricaprocaprylate, or vegetable oils or animal oils of formula $R_9COOR_{10}$ in which $R_9$ represents the residue of a higher fatty acid containing from 7 to 29 carbon atoms and $R_{10}$ represents a linear or branched hydrocarbon chain containing from 3 to 30 carbon atoms, in particular alkyl or alkenyl, for example Purcellin oil or liquid jojoba wax;
- natural or synthetic essential oils such as, for example, eucalyptus, lavender, lavandin, vetiver, litsea cubeba, lemon, sandalwood, rosemary, camomile, savory, nutmeg, cinnamon, hyssop, caraway, orange, geraniol, cade and bergamot oils;
- hydrocarbons such as hexadecane, branched or unbranched, and paraffin oil;
- halogenated hydrocarbons, in particular fluorocarbons such as fluoroamines, for example perfluorotributylamine, fluorinated hydrocarbons, for example perfluorodecahydronaphthalene, fluoroesters and fluoroethers;
- esters of an inorganic acid and an alcohol;
- ethers and polyethers;
- nonaminated silicones mixed with at least one of the oils defined above, for example decamethylcyclopentasiloxane or dodecamethylcyclohexasiloxane.

The emulsions in accordance with the present invention may contain additives for enhancing, if necessary, the transparency of the formulation.

These additives are preferably selected from:

$C_1$–$C_8$ lower alcohols such as ethanol;

glycols such as glycerin, propylene glycol, 1,3-butylene glycol, dipropylene glycol, polyethylene glycols containing from 4 to 16 ethylene oxide units and preferably from 8 to 12.

These additives, such as those mentioned above, are present in the emulsions of the invention in an amount preferably ranging from 1 to 30% by weight relative to the total weight of the emulsion.

In addition, the use of the alcohols as defined above, at concentrations greater than or equal to 5% by weight and preferably greater than 10% by weight makes it possible to obtain emulsions without a preservative.

The emulsions of the invention may contain water-soluble or fat-soluble active agents having a cosmetic or dermopharmaceutical activity.—The fat-soluble active agents are in the oily globules of the emulsion, whereas the water-soluble active agents are in the aqueous phase of the emulsion. There may be mentioned, by way of examples of active agent, vitamins such as vitamin E and derivatives thereof, provitamins such as panthenol, humectants, sunscreens containing silicone or not, surfactants, preservatives, sequestrants, emollients, perfumes, colorants, viscosity-modifying agents, foam-modifying agents, foam stabilizers, pearlescent agents, pigments, moisturizing agents, antidandruff agents, antiseborrhoeic agents, proteins, silicones, ceramides, pseudoceramides, fatty acids containing linear or branched $C_{16}$–$C_{40}$ chains such as 18-methyleicosanoic acid, thickeners, plasticizers, hydroxy acids, electrolytes, and polymers, in particular cationic polymers.

Among the thickeners which can be used, there may be mentioned cellulose derivatives such as hydroxymethylpropylcellulose, fatty alcohols such as stearyl, cetyl and behenyl alcohols, algal derivatives such as satia gum, natural gums such as tragacanth and synthetic polymers such as the polycarboxyvinyl acid mixtures marketed under the name CARBOPOL by the company GOODRICH and the Na acrylate/acrylamide copolymer mixture marketed under the name HOSTACERIN PN -73 by the company HOECHST.

The oil globules of the emulsions of the invention preferably have a mean size ranging from 30 to 150 nm, more preferably from 40 to 100 nm and still more preferably from 50 to 80 nm.

The emulsions of the invention may be obtained by a process characterized in that the aqueous phase, the oily phase and the amphiphilic lipids are mixed, with vigorous stirring, at an ambient temperature of less than 45° C. and in that a high-pressure homogenization is then carried out at a pressure greater than $10^8$ Pa and preferably ranging from $12 \times 10^7$ to $18 \times 10^7$ Pa. Such a process makes it possible to produce, at ambient temperature, nanoemulsions which are compatible with heat-sensitive active compounds and which may contain large quantities of oils and in particular perfumes which contain fatty substances, without denaturing them.

Another subject of the invention involves a composition for topical use, such as a cosmetic or dermopharmaceutical composition, characterized in that it is an emulsion as defined above or in that it comprises such an emulsion. The invention more particularly relates to hair compositions.

The compositions in accordance with the invention can be used for washing and cleansing keratinous materials such as hair and the skin.

The compositions can for example be used for cleansing or removing make-up from the skin.

The compositions of the invention can more particularly be provided in the form of a shampoo, a rinse-off or leave-in conditioner, compositions for permanent waving, hair straightening, dyeing or bleaching, or alternatively in the form of compositions to be applied before or after dyeing, bleaching, permanent waving or hair straightening or alternatively between the two stages of permanent waving or of hair straightening.

The compositions may also be hairsetting lotions, blow-drying lotions, fixing compositions (lacquers) and hair-styling compositions such as for example gels, or foams. The lotions may be packaged in various forms, particularly in vaporizers, pump dispensers or in aerosol containers in order to ensure application of the composition in vaporized form or in foam form. Such packaging forms are advisable, for example, when it is desired to obtain a spray, a lacquer or a foam for fixing or treating the hair.

The compositions may also be make-up compositions such as foundations, tinted day creams, mascaras, blushers, eyeshadows, lip compositions, and nail varnishes.

When the composition according to the invention is packaged in aerosol form in order to obtain a lacquer or an aerosol foam, it comprises at least one propellent which may be selected from volatile hydrocarbons such as n-butane, propane, isobutane, pentane, chlorinated and/or fluorinated hydrocarbons and mixtures thereof. It is also possible to use, as propellent, carbon dioxide, nitrous oxide, dimethyl ether, nitrogen or compressed air.

Another subject of the invention is the use of the emulsions as defined above as base for treatment and/or make-up and/or make-up removing products for the skin and/or the face and/or the scalp and/or the hair and/or the nails and/or the eyelashes and/or the eyebrows and/or the mucous membranes (for example the lips), such as lotions, serums, milks, creams, and toilet water.

Finally, the invention also relates to a nontherapeutic process for treating the skin, the hair, the eyelashes, the eyebrows, the nails, the mucous membranes; or the scalp, characterized in that an emulsion or a composition as defined above is applied to the skin, the hair, the eyelashes, the eyebrows, the nails, the mucous membranes or to the scalp.

The following examples will make it possible to understand the invention more clearly without, however, being limiting in any way.

EXAMPLES

For Examples 1 and 7, the following procedure was used:

The ingredients were mixed with the aid of a turbine homogenizer and then homogenized with the aid of a Soavi-Niro type high-pressure homogenizer at a pressure of about 1200 bar, in several passes (4 to 8) while maintaining the temperature of the product below about 35° C.

Example 1

A conditioner having the following composition was prepared:

Polyethylene glycol isostearate (8EO) marketed by the company UNICHEMA under the name ESTOL B UCN PEG-400 monoisostéarate BIO 4.5 g Behenyltrimethylammonium chloride (cationic amphiphilic lipid) 1.6 gAI Avocado oil 15 g Amodimethicone in emulsion marketed under the name DC2-8902 by the company DOW CORNING 1.75 gAI Absolute ethanol 15 g Glycerin 5 g Demineralized water qs 100 g An emulsion was obtained in which the size of the oil globules was about 95 nm.

This composition was applied to wet hair. After rinsing with water, the hair thus treated was soft and sleek.

Example 2

A conditioner having the following composition was prepared:

Polyethylene glycol isostearate (8EO) marketed by the company UNICHEMA under the name ESTOL B UCN PEG-400 monoisostéarate BIO 4.5 g Behenyltrimethylammonium chloride (cationic amphiphilic lipid) 0.8 gAI Avocado oil 20 g Polydimethylsiloxane with $\alpha,\omega$-quaternary ammonium groups marketed under the name ABIL QUAT 3474 by the company GOLDSCHMIDT 1.9 gAI Tocopherol acetate 1 g Absolute ethanol 15 g Glycerin 5 g Demineralized water qs 100 g An emulsion was obtained in which the size of the oil globules was about 79 nm.

This composition was applied to wet hair. The hair thus treated was soft, sleek and easy to disentangle.

Example 3

A conditioner having the following composition was prepared:

Polyethylene glycol isostearate (8EO) marketed by the company UNICHEMA under the name ESTOL B UCN PEG-400 monoisostéarate BIO 4.5 g Behenyltrimethylammonium chloride (cationic amphiphilic lipid) 0.8 gAI Avocado oil 20 g Polydimethylsiloxane with $\alpha,\omega$-quaternary ammonium groups marketed under the name ABIL QUAT 3272 by the company GOLDSCHMIDT 1 gAI Tocopherol acetate 1 g Absolute ethanol 15 g Glycerin 5 g Demineralized water qs 100 g An emulsion was obtained in which the size of the oil globules was about 62 nm.

This composition was applied to wet hair. The hair thus treated was soft, sleek and easy to disentangle.

Example 4

A conditioner having the following composition was prepared:

Polyethylene glycol isostearate (8EO) marketed by the company UNICHEMA under the name ESTOL B UCN PEG-400 monoisostéarate BIO 4.5 g Behenyltrimethylammonium chloride (cationic amphiphilic lipid) 0.8 gAl Liquid jojoba wax 17 g Polydimethylsiloxane with α,ω-quaternary ammonium groups marketed under the name ABIL QUAT 3474 by the company GOLDSCHMIDT 1.9 gAl Tocopherol acetate 1 g Isohexadecane 3 g Absolute ethanol 15 g Glycerin 5 g Demineralized water qs 100 g An emulsion was obtained in which the size of the oil globules was about 79 nm.

This composition was applied to wet hair. The hair thus treated was soft, sleek and easy to disentangle.

Example 5

A conditioner having the following composition was prepared:

Polyethylene glycol isostearate (8EO) marketed by the company UNICHEMA under the name ESTOL B UCN PEG-400 monoisostéarate BIO 4.5 g Behenyltrimethylammonium chloride (cationic amphiphilic lipid) 1.6 gAl Avocado oil 14 g Microemulsion of trimethysilyl amodimethicone marketed under the name SM 2115 by the company GENERAL ELECTRIC 1.2 gAl Absolute ethanol 15 g Glycerin 5 g Demineralized water qs 100 g An emulsion was obtained in which the size of the oil globules was about 70 nm.

This composition was applied to wet hair. The hair thus treated was soft, sleek and easy to disentangle.

Example 6

A conditioner having the following composition was prepared:

Polyethylene glycol isostearate (8EO) marketed by the company UNICHEMA under the name ESTOL B UCN PEG-400 monoisostéarate BIO 4.5 g Behenyltrimethylammonium chloride (cationic amphiphilic lipid) 0.8 gAl Liquid jojoba wax 5.25 g Avocado oil 5.25 g Polydimethylsiloxane with α,ω-quaternary ammonium groups marketed under the name ABIL QUAT 3272 by the company GOLDSCHMIDT 1 gAl Cyclomethicone marketed by the company DOW CORNING under the name DC245 FLUID 3.5 g Absolute ethanol 15 g Glycerin 5 g Demineralized water qs 100 g An emulsion was obtained in which the size of the oil globules was about 48 nm.

This composition was applied to wet hair. The hair thus treated was soft, sleek and easy to disentangle Example 7

A conditioner having the following composition was prepared:

Polyethylene glycol isostearate (8EO) marketed by the company UNICHEMA under the name ESTOL B UCN PEG-400 monoisostéarate BIO 4.5 g Behenyltrimethylammonium chloride (cationic amphiphilic lipid) 1.6 gAl Liquid jojoba wax 20 g ammonium groups marketed under the name ABIL QUAT 3474 by the company GOLDSCHMIDT 0.95 gAl Polydimethylsiloxane with α,ω-quaternary ammonium groups marketed under the name ABIL QUAT 3272 by the company GOLDSCHMIDT 0.5 gAl Tocopherol acetate 1 g Absolute ethanol 15 g Glycerin 5 g Demineralized water qs 100 g An emulsion was obtained in which the size of the oil globules was about 54 nm.

This composition was applied to wet hair. The hair thus treated was soft, sleek and easy to disentangle.

We claim:

1. An oil-in-water emulsion comprising:

at least one oil, wherein said at least one oil is present in an oily phase dispersed in an aqueous phase and comprises oil globules with a mean size no greater than 150 nm, at least one aminated silicone, an amphiphilic lipid phase comprising at least one nonionic amphiphilic lipid which is liquid at an ambient temperature of less than 45° C., wherein the weight ratio of said oily phase to said amphiphilic lipid phase ranges from 2:1 to 10:1, and wherein said at least one nonionic amphiphilic lipid is selected from silicone surfactants and esters of: at least one polyol selected from polyethylene glycol containing 1 to 60 ethylene oxide units, sorbitan, glycerol containing from 2 to 30 ethylene oxide units, and polyglycerols containing from 2 to 15 glycerol units, and at least one fatty acid containing at least one saturated or unsaturated linear or branched $C_8$–$C_{22}$ alkyl chain, and further wherein said at least one oil is selected from the animal or vegetable oils formed by esters of fatty acids and of polyols, vegetable oils and animal oils of formula $R_9COOR_{10}$ in which $R_9$ represents the residue of a higher fatty acid containing from 7 to 29 carbon atoms and $R_{10}$ represents a linear or branched hydrocarbon chain containing from 3 to 30 carbon atoms;

natural or synthetic essential oils;

hydrocarbons;

halogenated hydrocarbons;

esters of an inorganic acid and an alcohol;

ethers and polyethers;

nonaminated silicones mixed with at least one oil listed herein.

2. An oil-in-water emulsion according to claim 1, wherein said weight ratio ranges from 2:1 to 8:1.

3. An oil-in-water emulsion according to claim 2, wherein said weight ratio ranges from 2:1 to 6:1.

4. An oil-in-water emulsion according to claim 1, wherein said silicone surfactants are selected from compounds of formula (I):

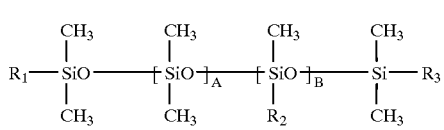
(I)

in which:

R₁, R₂, and R₃ independently represent a $C_1$–$C_6$ alkyl radical or a radical —$(CH_2)_x$—$(OCH_2CH_2)_y$—$(OCH_2CH_2CH_2)_z$—$OR_4$, wherein $R_4$ is selected from hydrogen, an alkyl radical and an acyl radical, and wherein at least one R₁, R₂, or R₃ radical is not an alkyl radical;

A is an integer ranging from 0 to 200;

B is an integer ranging from 0 to 50;

with the proviso that A and B are not simultaneously equal to 0;

X is independently an integer ranging from 1 to 6;

Y is independently an integer ranging from 1 to 30; and

Z is independently an integer ranging from 0 to 5.

5. An oil-in-water emulsion according to claim 4, wherein in said compound of formula (I), said alkyl radical is a methyl radical, X is an integer independently ranging from 2 to 6 and Y is an integer independently ranging from 4 to 30.

6. An oil-in-water emulsion according to claim 1, wherein said silicone surfactants are selected from compounds of formula (II):

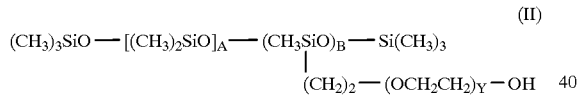
(II)

in which:

A is an integer ranging from 20 to 105;

B is an integer ranging from 2 to 10; and

Y is an integer ranging from 10 to 20.

7. An oil-in-water emulsion according to claim 1, wherein said silicone surfactants are selected from compounds of formula (III):

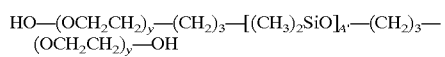
(III)

in which:

A' and Y independently represent an integer ranging from 10 to 20.

8. An oil-in-water emulsion according to claim 1, wherein said at least one aminated silicone is selected from:

(a) polysiloxanes called in the CFTA dictionary "amodimethicone" and corresponding to formula (IV):

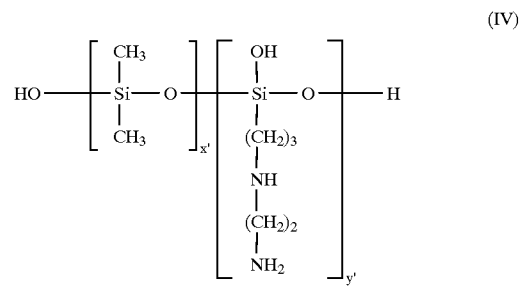
(IV)

in which:

x' and y' independently are integers resulting in a weight-average molecular weight ranging from 5000 to 500,000;

(b) aminated silicones corresponding to formula (V):

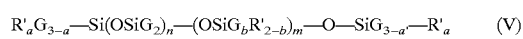
(V)

in which:

G independently denotes a hydrogen atom or a phenyl, OH or $C_1$–$C_8$ alkyl;

a denotes the number 0 or an integer ranging 1 to 3;

b denotes 0 or 1;

m and n are numbers such that the sum (m+n) varies from 1 to 2000, n denotes a number from 0 to 1999 and m denotes a number from 1 to 2000;

R' is independently a monovalent radical of formula —$C_qCH_{2q}L$ in which q denotes a number from 2 to 8 and L is an optionally quaternized amine group selected from:

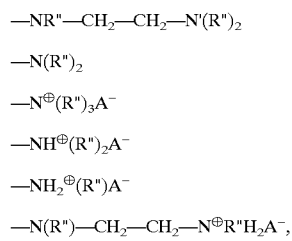

in which:

R" denotes hydrogen, phenyl, benzyl or a monovalent saturated hydrocarbon radical, and A⁻ represents a halide ion, (c) aminated silicones corresponding to formula (VII):

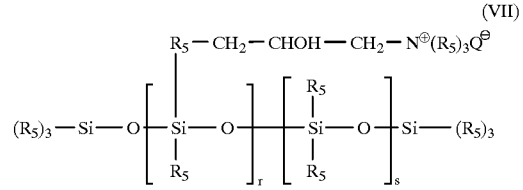
(VII)

in which:

R₅ independently represents a monovalent hydrocarbon radical having from 1 to 18 carbon atoms;

R₆ independently represents a divalent hydrocarbon radical or a divalent $C_1$–$C_{18}$ alkyleneoxy radical;

Q⁻ is an anion;

r represents a mean statistical value from 2 to 20; and s represents a mean statistical value from 20 to 200, (d) quaternary ammonium silicones of formula (VIIb)

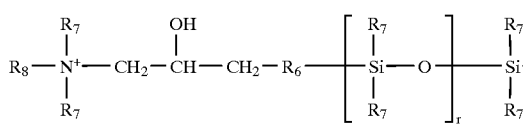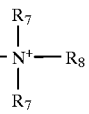

(VIIb)

in which:

R₇ independently represents a monovalent hydrocarbon radical having from 1 to 18 carbon atoms, or a ring comprising 5 or 6 carbon atoms;

R₆ independently represents a divalent hydrocarbon radical or a divalent $C_1$–$C_{18}$ alkyleneoxy radical;

R₈ independently represents a hydrogen atom, a monovalent hydrocarbon radical having from 1 to 18 carbon atoms, or a radical —R₆NHCOR₇;

X⁻ is an anion; and r represents a mean statistical value from 2 to 200.

9. An oil-in-water emulsion according to claim 8, wherein at least one of the following is true:

in formula (V), G is a methyl group; a is 0; b is 1; the sum (m+n) varies from 50 to 150; n denotes a number from 49 to 149; m denotes a number from 1 to 10;

R" denotes an alkyl radical having from 1 to 20 carbon atoms; and A⁻ represents fluoride, chloride, bromide or iodide.

10. An oil-in-water emulsion according to claim 8, wherein at least one of the following is true:

in formula (VII), R₅ independently represents a $C_1$–$C_{18}$ alkyl radical or a $C_2$–$C_{18}$ alkenyl radical;

R₆ independently represents a $C_1$–$C_{18}$ alkylene radical;

Q⁻ is a halide anion or an organic acid salt;

r represents a mean statistical value from 2 to 8; and s represents a mean statistical value from 20 to 50.

11. An oil-in-water emulsion according to claim 10, wherein at least one of the following is true:

R₅ represents methyl; and

R₆ represents a $C_1$–$C_8$ alkylene radical linked to Si by an SiC bond; and

Q⁻ is a chloride anion or an acetate.

12. An oil-in-water emulsion according to claim 8, wherein at least one of the following is true:

in formula VIIb, R₇ independently represents a $C_1$–$C_{18}$ alkyl radical, or a $C_2$–$C_{18}$ alkenyl radical;

R₆ independently represents a $C_1$–$C_{18}$ alkylene radical;

R₈ independently represents a $C_1$–$C_{18}$ alkyl radical, or a $C_2$–$C_{18}$ alkenyl radical;

X⁻ is a halide anion or an organic acid salt;

r represents a mean statistical value from 5 to 100.

13. An oil-in-water emulsion according to claim 12, wherein at least one of the following is true:

R₇ is methyl;

R₆ represents a $C_1$–$C_8$ alkylene radical linked to Si by an SiC bond; and

X⁻ is a chloride anion or an acetate.

14. An oil-in-water emulsion according to claim 1, wherein said at least one aminated silicone is present in an amount ranging from 0.05 to 10% by weight, relative to the total weight of said emulsion.

15. An oil-in-water emulsion according to claim 14, wherein said at least one aminated silicone is present in an amount ranging from 0.1 to 5% by weight, relative to the total weight of said emulsion.

16. An oil-in-water emulsion according to claim 15, wherein said at least one aminated silicone is present in an amount ranging from 0.3 to 3% by weight, relative to the total weight of said emulsion.

17. An oil-in-water emulsion according to claim 1, wherein said emulsion further comprises at least one ionic amphiphilic lipid.

18. An oil-in-water emulsion according to claim 17, wherein said at least one ionic amphiphilic lipid is selected from anionic lipids, amphoteric lipids and cationic lipids.

19. An oil-in-water emulsion according to claim 18, wherein said cationic lipids are selected from quaternary ammonium salts and fatty amines and salts thereof.

20. An oil-in-water emulsion according to claim 19, wherein said quaternary ammonium salts are selected from:

quaternary salts of formula (VIII):

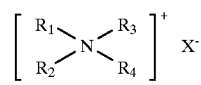

(VIII)

in which:

the radicals R₁ to R₄ independently represent a linear or branched aliphatic radical containing from 1 to 30 carbon atoms, or an aromatic radical;

X is an anion selected from halides, phosphates, acetates, lactates, ($C_2$–$C_6$)alkyl sulphates and alkyl- and alkylarylsulphonates, the quaternary ammonium salts of imidazolinium;

the quaternary diammonium salts of formula (X):

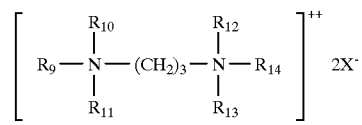

(X)

in which:

R₉ designates an aliphatic radical containing from about 16 to 30 carbon atoms,

R₁₀, R₁₁, R₁₂, R₁₃, and R₁₄ independently are selected from hydrogen and an alkyl radical containing from 1 to 4 carbon atoms, and X is an anion selected from halides, acetates, phosphates, nitrate and methyl sulphates, and the quaternary ammonium salts containing at least one ester functional group.

21. An oil-in-water emulsion according to claim 1, wherein said amphiphilic lipid phase further comprises at least one ionic amphiphilic lipid in an amount ranging up to 60% by weight relative to the total weight of said amphiphilic lipid phase.

22. An oil-in-water emulsion according to claim 4, wherein said at least one ionic amphiphilic lipid is present in an amount ranging from 10 to 50% by weight relative to the total weight of said amphiphilic lipid phase.

23. An oil-in-water emulsion according to claim 1, wherein said amphiphilic lipid phase further comprises at least one ionic amphiphilic lipid in an amount ranging up to 10% by weight relative to the total weight of said emulsion.

24. An oil-in-water emulsion according to claim 23, wherein said at least one ionic amphiphilic lipid is present in an amount ranging from 0.05 to 5% by weight relative to the total weight of said emulsion.

25. An oil-in-water emulsion according to claim 24, wherein said at least one ionic amphiphilic lipid is present in an amount ranging from 0.5 to 3% by weight relative to the total weight of said emulsion.

26. An oil-in-water emulsion according to claim 1, wherein said at least one oil is present in an amount ranging from 5 to 40% by weight relative to the total weight of said emulsion.

27. An oil-in-water emulsion according to claim 26, wherein said at least one oil is present in an amount ranging from 8 to 30% by weight relative to the total weight of said emulsion.

28. An oil-in-water emulsion according to claim 1, wherein said emulsion further comprises a water-soluble or fat-soluble cosmetic or dermopharmaceutical active agent.

29. A composition comprising an oil-in-water emulsion according to claim 1.

30. An oil-in-water emulsion according to claim 1, wherein said oil globules have a mean size ranging from 30 to 150 nm.

31. An oil-in-water emulsion according to claim 30, wherein said oil globules have a mean size ranging from 40 to 100 nm.

32. An oil-in-water emulsion according to claim 31, wherein said oil globules have a mean size ranging from 50 to 80 nm.

33. A method for preparing an emulsion according to claim 1 comprising: mixing said aqueous phase, said oily phase and said at least one amphiphilic lipid, at an ambient temperature of less than 45° C.; and carrying out homogenization at a pressure greater than $10^8$ Pa.

34. A method according to claim 33, wherein said pressure ranges from $12 \times 10^7$ to $18 \times 10^7$ Pa.

35. A composition according to claim 29, wherein said composition is a hair composition.

36. A composition according to claim 29, wherein said composition is a composition for washing and/or treating keratinous materials or a composition for cleansing or removing make-up from the skin.

37. A composition according to claim 29, wherein said composition is in the form of a shampoo; a rinse-off or leave-in conditioner; hairsetting lotion; blow-drying lotion; fixing composition (lacquer); hair-styling composition; composition for permanent waving, hair straightening, dyeing or bleaching; a composition to be applied before or after dyeing, bleaching, permanent waving or hair straightening; or a composition to be applied between the two stages of permanent waving or of hair straightening.

38. A nontherapeutic process for treating the skin, the hair, the eyelashes, the eyebrows, the nails, the mucous membranes, or the scalp, comprising applying an effective amount of an emulsion according to claim 1 to said skin, hair, eyelashes, eyebrows, nails, mucous membranes or scalp.

39. A nontherapeutic process for treating the skin, the hair, the eyelashes, the eyebrows, the nails, the mucous membranes, or the scalp, comprising applying an effective amount of at least one composition according to claim 29 to said skin, hair, eyelashes, eyebrows, nails, mucous membranes or scalp.

* * * * *

UNITED STATES PATENT AND TRADEMARK OFFICE
CERTIFICATE OF CORRECTION

PATENT NO.: 5,925,341

DATED: July 20, 1999

INVENTOR(S): Frédéric CERVANTES; Bénédicte CAZIN; and Jean-Thierry SIMONNET

It is certified that an error appears in the above-identified patent and that said Letters Patent is hereby corrected as shown below:

<u>IN THE CLAIMS</u>:

Claim 1, col. 16, lines 58-59, replace "nonaminated silicones mixed with at least one oil listed herein" with --at least one of the above oils mixed with at least one nonaminated silicone--.

Claim 22, col. 21, line 10, "claim 4" should read --claim 21--.

Signed and Sealed this

Twenty-eighth Day of December, 1999

Attest:

Q. TODD DICKINSON

Attesting Officer

Acting Commissioner of Patents and Trademarks